United States Patent
Lee et al.

(10) Patent No.: US 9,726,788 B2
(45) Date of Patent: Aug. 8, 2017

(54) METHOD FOR FABRICATING NANOANTENNA ARRAY, NANOANTENNA ARRAY CHIP AND STRUCTURE FOR LITHOGRAPHY

(71) Applicant: KOREA INSTITUTE OF SCIENCE AND TECHNOLOGY, Seoul (KR)

(72) Inventors: Kyeong Seok Lee, Seoul (KR); Won Mok Kim, Seoul (KR); Taek Sung Lee, Seoul (KR); Wook Seong Lee, Seoul (KR); Doo Seok Jeong, Wonju-si (KR); Inho Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 167 days.

(21) Appl. No.: 14/253,522

(22) Filed: Apr. 15, 2014

(65) Prior Publication Data
US 2015/0146180 A1    May 28, 2015

(30) Foreign Application Priority Data

Nov. 22, 2013  (KR) ........................ 10-2013-0143068

(51) Int. Cl.
| | |
|---|---|
| *G03F 7/20* | (2006.01) |
| *G02B 5/00* | (2006.01) |
| *G01N 21/552* | (2014.01) |
| *B82Y 40/00* | (2011.01) |

(Continued)

(52) U.S. Cl.
CPC ............. *G02B 5/008* (2013.01); *B82Y 15/00* (2013.01); *B82Y 40/00* (2013.01); *G01N 21/554* (2013.01); *G03F 7/2014* (2013.01); *G03F 7/70375* (2013.01); *G02B 5/0278* (2013.01)

(58) Field of Classification Search
CPC .. G03F 7/70375; G03F 7/2051; G03F 7/2067; G02B 5/008; G02B 5/0278; G01N 21/54; B82Y 15/00; B82Y 20/00; B82Y 40/00
USPC ........ 430/315, 319, 321; 977/810, 893, 901, 977/954
See application file for complete search history.

(56) References Cited

U.S. PATENT DOCUMENTS

| | | | |
|---|---|---|---|
| 2010/0080954 | A1 | 4/2010 | Mohseni |
| 2012/0258289 | A1 | 10/2012 | Lee et al. |
| 2013/0148194 | A1 | 6/2013 | Altug et al. |

FOREIGN PATENT DOCUMENTS

| | | |
|---|---|---|
| KR | 10-2011-0032466 A | 3/2011 |
| KR | 10-2012-0113916 A | 10/2012 |
| WO | WO 2011/050272 A2 * | 4/2011 |

* cited by examiner

*Primary Examiner* — John A McPherson
(74) *Attorney, Agent, or Firm* — NSIP Law

(57) ABSTRACT

A method for fabricating a nanoantenna array may include forming a resist layer on a substrate, forming a focusing layer having a dielectric microstructure array on the resist layer, diffusing light one-dimensionally in a specific direction by using a linear diffuser, forming an anisotropic pattern on the resist layer by illuminating the light diffused by the linear diffuser on the focusing layer and the resist layer, depositing a material suitable for a plasmonic resonance onto the substrate and the resist layer on which the pattern is formed, and forming a nanoantenna array on the substrate by removing the resist layer and the material deposited on the resist layer. A light diffusing angle by the linear diffuser and a size of the dielectric microstructure are determined based on an aspect ratio of the pattern to be formed.

18 Claims, 14 Drawing Sheets

(51) Int. Cl.
*B82Y 15/00* (2011.01)
*G02B 5/02* (2006.01)

METHOD FOR FABRICATING NANOANTENNA ARRAY, NANOANTENNA ARRAY CHIP AND STRUCTURE FOR LITHOGRAPHY

CROSS-REFERENCE TO RELATED APPLICATION

This application claims priority to Korean Patent Application No. 10-2013-0143068, filed on Nov. 22, 2013, and all the benefits accruing therefrom under 35 U.S.C. §119, the contents of which in its entirety are herein incorporated by reference.

BACKGROUND

1. Field

Embodiments relate to a process for forming a nanoantenna array, a nanoantenna array chip and a structure for lithography, which is used for forming a nanoantenna array.

2. Description of the Related Art

A metallic nanostructure shows a localized surface plasmon resonance phenomenon in a specific wavelength region due to a dielectric confinement effect of free electrons. At a resonance wavelength, a local electric field near a metallic nanostructure is strongly enhanced, and a characteristic optical absorption or scattering behavior occurs in proportion to the intensity of the local electric field.

Since the characteristics of localized surface plasmon resonance sensitively depend on the change of surroundings, sensor application using the same has been extensively studied. For example, it is typical that the effect of local electric field enhancement is utilized in plasmonic substrates for a surface enhanced spectroscopy which amplify a Raman signal or a fluorescence signal arising from the molecules present near the metallic nanostructures, and a sensitive response of resonance wavelength to the change in an effective refractive index of surrounding media is used for a localized surface plasmon resonance sensor to detect an analyte near the metallic nanostructures.

Recently, an infrared plasmonic nanoantenna technology is in the spotlight for its potential to amplify a spectroscopic molecular absorption signal by matching the vibrational modes inherent to a molecule to be analyzed with a plasmonic mode of a metallic nanostructure or give a way of using a plasmon energy transition into the molecule, thereby enabling the highly sensitive and selective detection of analytes. Most molecules have inherent vibrational modes in the infrared wavelength region, but the infrared wavelength is much greater than the size of molecules. Thus, the molecular absorption coefficient in the infrared region is generally low. However, if the plasmonic nanoantennas are used, the size mismatch may be overcome by means of a local electric field concentrated on the surface of nanostructures, and thus infrared absorption signals of adjacent molecules may be amplified.

In this case, since most molecules have their inherent vibrational modes in an infrared wavelength region, specifically in a mid-infrared region between 2 µm and 20 µm called a molecular fingerprint region, as described above, the resonance wavelength of nanoantenna needs to be tailored in the infrared region to match the plasmonic modes of metallic nanostructures with the vibrational modes of a molecule to be analyzed. In order to facilitate the shift of resonance wavelength of nanoantennas to the infrared region, the nanostructures should have an anisotropic shape, and particularly in the case of a nanorod structure known for its excellent wavelength tunability, the aspect ratio which is a ratio of long axis to short axis needs to be increased.

Plasmonic infrared nanoantennas reported until now have been mostly fabricated using E-beam lithography. The E-beam lithography has an advantage in that a nanostructure of a desired shape may be precisely fabricated, but it requires expensive processing equipment and is not suitable for fabricating a large-area array chip due to its low throughput. Meanwhile, nanoimprint lithography may resolve the issue of low-throughput of the traditional E-beam lithography by repeatedly replicating nanopatterns with a stamper. Even in this case, however, fabrication of the stamper still relies on the E-beam lithography that is expensive and time-consuming, and once the stamper pattern is fixed, versatile modification in the pattern is impossible. Also, the pressure and temperature must be kept uniform throughout the imprinting process. Therefore, this method still has limitations in terms of overall costs and large-area processing.

As an alternative, U.S. Patent Publication No. 2013/0148194 discloses a method for forming a plasmonic nanoantenna using a nanostencil lithography. In this method, an array of nanostructures can be simply transferred onto a substrate just by depositing a target material over a free-standing stencil mask precisely perforated to have nanopattern pores, similar to a traditional stencil printing method. This process itself is simpler than the nanoimprint method, but it requires both an expensive E-beam lithography and a micro-electromechanical system (MEMS) process to make the nanostencil mask. In addition, it is impossible to give a modification in structure, other than a given pattern, and not suitable for a large-area process due to the free standing structure of nanostencil.

The resonance wavelength of a nanoantenna may be easily tailored to match the inherent vibrational modes of molecules constituting an analyte by controlling a shape of the nanoantenna. Therefore, there exists a need for a low cost process for a large area fabrication of nanoantenna arrays which enables a versatile control of the resonance wavelength on request.

U.S. Unexamined Patent Publication No. 2012/0258289 discloses a method for fabricating an array of anisotropic nanostructures based on a low cost self-assembly process. This method makes it possible to fabricate anisotropic nanostructures by modifying an existing patterning process which utilizes a photonic nanojet, generated when a transparent dielectric micro-bead is illuminated by light and having a sub-diffraction-limit spot size, to sensitize a photoresist located below the dielectric micro-bead. In detail, by adding a linear diffuser which scatters light only in one direction, the focused light forms an anisotropic spot pattern on the photoresist layer and finally a nanorod type structure is implemented. This document discloses a method for adjusting a divergence angle of the diffuser to increase an aspect ratio of the nanorod but does not disclose a method for accomplishing the aspect ratio high enough to shift the resonance wavelength to cover an infrared region of 2 µm to 20 µm for the application into an infrared nanoantenna and various structural engineering techniques for improving functionality of the nanoantenna.

SUMMARY

An aspect of the present disclosure may provide a method for fabricating a nanoantenna array which has a plasmonic resonance wavelength in an infrared region, and a nanoantenna array chip fabricated by the method. The method may enhance the degree of freedom for shape control of a nanostructure array by an inexpensive and simple process. In addition, according to an aspect of the present disclosure, a structure for lithography, which is used for fabricating a nanoantenna array, may be provided. Further, an aspect of the present disclosure may provide a plasmonic infrared nanoantenna array chip which is polarization independent and has an increased effective density of nanoantennas per unit area.

According to an embodiment, a method for fabricating a nanoantenna array may include: forming a resist layer on a substrate; forming a focusing layer having a dielectric microstructure array on the resist layer; diffusing light one-dimensionally in a specific direction by using a linear diffuser; forming an anisotropic pattern on the resist layer by illuminating the light diffused by the linear diffuser on the focusing layer and the resist layer; depositing a material suitable for plasmonic resonance onto the substrate and the patterned resist layer; and forming a nanoantenna array on the substrate by removing the resist layer and the material deposited on the resist layer, wherein a light diffusing angle of the linear diffuser and a size of the dielectric microstructure may be determined based on an aspect ratio of the pattern to be formed, is provided.

In the method for fabricating a nanoantenna array according to an embodiment, the process step of diffusing light one-dimensionally in a specific direction and forming the anisotropic patterns on the resist layer may be repeated several times, and the light diffusing direction by the linear diffuser may be changed in each turn.

According to an embodiment, a nanoantenna array chip may be fabricated by forming a resist layer on a substrate; forming a focusing layer having a dielectric microstructure array on the resist layer; diffusing light one-dimensionally in a specific direction by using a linear diffuser; forming an anisotropic pattern on the resist layer by illuminating the light diffused by the linear diffuser on the focusing layer and the resist layer; depositing a material suitable for a plasmonic resonance onto the substrate and the patterned resist layer; and forming a nanoantenna array on the substrate by removing the resist layer and the material deposited on the resist layer, wherein a light diffusing angle of the linear diffuser and a size of the dielectric microstructure may be determined based on an aspect ratio of a pattern to be formed, is provided.

According to another embodiment, a structure for lithography may include: a linear diffuser configured to diffuse light one-dimensionally in a specific direction; a focusing layer including a dielectric microstructure array and configured to focus the light diffused by the linear diffuser; and a resist layer located under the focusing layer so that the resist layer can be sensitized by the light focused passing through the focusing layer and an anisotropic pattern may be formed with an aspect ratio determined based on a light diffusing angle of the linear diffuser and a size of the dielectric microstructure, wherein the dielectric microstructure has a diameter of 1 μm to 10 μm, is provided.

According to the method for fabricating a nanoantenna array according to an aspect of the present disclosure, an infrared nanoantenna array showing a plasmonic resonance characteristic in an infrared wavelength region of 2 μm to 20 μm where most molecules have their inherent vibrational modes may be easily implemented. Since the infrared nanoantenna array is based on a localized surface plasmon which is excited in an infrared wavelength region where the free electron behavior of metals becomes dominant, the enhancement of local electric field and the sensitivity to the change of surrounding environments may be improved further. By matching the resonance wavelength of the plasmonic nanoantenna with the inherent vibrational modes of a target molecule to be analyzed, the nanoantenna array may be used as a plasmonic substrate for greatly amplifying the surface enhanced infrared absorption signal or for molecular fingerprinting spectroscopy based on the energy transfer between plasmon and molecules. In addition, the nanoantenna array may be utilized as a localized surface plasmon resonance sensor for detecting an analyte by means of a resonance wavelength shift which sensitively responds to the change of effective refractive index of surrounding medium, and the infrared nanoantenna array may allow a cell-based analysis because the decay length of surface plasmon into the medium increases to the level of microns.

In addition, according to the method for fabricating a nanoantenna array according to an embodiment of the present disclosure, by applying a multiple exposure process, an infrared nanoantenna array chip which is polarization independent and has an increased effective density of nanoantennas per unit area may be implemented. Therefore the plasmonic signal may be improved further and an expensive infrared polarizer does not need to be used in actual application.

BRIEF DESCRIPTION OF THE DRAWINGS

The above and other aspects, features and advantages of the disclosed exemplary embodiments will be more apparent from the following detailed description taken in conjunction with the accompanying drawings in which:

FIG. 12 is a SEM image showing the nanostar type Au nanoantenna array having the structure illustrated in FIG. 11a;

DETAILED DESCRIPTION

Hereinafter, embodiments of the present disclosure will be described in detail with reference to the accompanying drawings.

Figure 1:
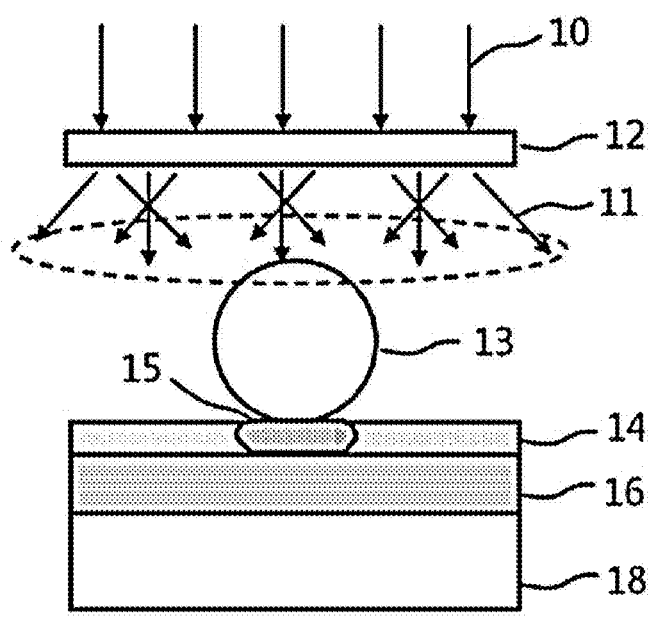
FIG. 1 is a schematic diagram showing an exemplary processing unit for performing a nanoantenna array fabricating method according to an embodiment of the present disclosure.

FIG. 1 is a schematic diagram showing an exemplary processing unit for performing a method for fabricating a nanoantenna array (hereinafter, also referred to as a nanoantenna array fabricating method) according to an embodiment of the present disclosure. The processing unit may be a structure for lithography according to an embodiment of the present disclosure, and the structure for lithography may include a linear diffuser 12, a focusing layer having an array of dielectric microstructures 13 and a resist layer 14.

Referring to FIG. 1, the nanoantenna array fabricating method according to an embodiment will be described. First, the resist layer 14 is formed on a substrate 18. The resist layer 14 may be configured to have a dual-layered structure having an additional lower undercut-forming layer 16, which is etched by most developing solutions, as shown in FIG. 1 in order to facilitate a following lift-off process. After that, the focusing layer having an array of dielectric microstructures 13 is formed on the resist layer 14. Then, the incident light 10 is diffused one-dimensionally in a specific direction by using the linear diffuser 12, and the light 11 diffused by the linear diffuser 12 is illuminated on the dielectric microstructures 13 and the resist layer 14.

The focusing layer having an array of dielectric microstructures 13 focuses the light 10, illuminated in the exposure process, on the resist layer 14 in the form of a photonic nanojet having a full width at half maximum (FWHM) of sub-diffraction limit. Here, the FWHM means a spatial distance between positions at focused spot at which the amplitude of electric field of light is equal to half of its maximum. Due to the difference in exposure dose between the focused region and surrounding regions, the resist layer 14 is selectively sensitized and a pattern 15 is formed at the resist layer 14. The sensitized region shows a two-dimensional array identical to the array of dielectric microstructures 13 constituting the focusing layer. After the pattern 15 is formed at the resist layer 14, a material suitable for plasmonic resonance is deposited on the patterned resist 14 and the substrate 18 through openings created in the resist layer 14, and a nanoantenna array may be formed on the substrate 18 by removing the resist layer 14 and the material deposited on the resist layer 14.

The dielectric microstructure 13 of the focusing layer may be made of a material which is transparent or has low optical absorption at a wavelength of light used for the exposure process. In an embodiment, the dielectric microstructure 13 has a spherical shape. The array of dielectric microstructures 13 may be formed as a monolayer with a regular hexagonal close-packed structure by using a self-assembly process. On occasions, a focusing layer, in which regularly arrayed dielectric microstructures, i.e. dielectric beads having a high refractive index are embedded in a polymer membrane with a relatively low refractive index, may also be used for repeated use.

The resist layer 14 may be a photoresist which is sensitized by light or a thermal resist which undergoes a phase transition by heat generated during a light absorbing process.

The substrate 18 may be made of a material which is generally transparent or has low optical absorption in the infrared wavelength region for the application to a plasmonic nanoantenna array chip operating in the infrared region. For example, the substrate 18 may be made of sapphire, $CaF_2$, $MgF_2$, ZnSe, Si, $Si_3N_4$, Ge, GaAs, $SiO_2$, KBr, diamond or polymer.

The material of the plasmonic nanoantenna may be a material whose optical behavior in the infrared wavelength region is described with a free electron model, for example, Au, Ag, Cu, Al, Pt, Pd, Ni, Co, Fe, Mn, Cr, Mo, W, V, Ta, Nb, Sn, Pb, Sb, Bi or their alloys. In addition, the nanoantenna may be made of semiconducting materials having a free electron density of $10^{-20}$ $cm^{-3}$ or above, for example, transparent conductive oxides, nitrides or degenerated semiconductors.

In the nanoantenna array fabricating method, if the linear diffuser 12 is configured to diffuse the incident light 10 one-dimensionally in a specific direction with a predetermined angular divergence and keep collimation in a direction perpendicular thereto, the linearly diffused light 11 forms an anisotropic focal spot when passing through the focusing layer, and thus forms an anisotropic pattern 15 at the resist layer 14 located underneath. Since the aspect ratio of the anisotropic pattern 15 greatly depends on not only the light diffusing angle by the linear diffuser 12 but also a diameter of the dielectric microstructure 13 of the focusing layer, the light diffusing angle of the linear diffuser 12 and the size of the dielectric microstructure 13 may be determined based on the aspect ratio of the pattern 15 to be formed. The diameter of the dielectric microstructure 13 may be 1 µm to 10 µm, and the nanoantenna fabricated following the aspect ratio of the formed pattern 15 may have a resonance wavelength of 2 µm to 20 µm.

Figure 2:
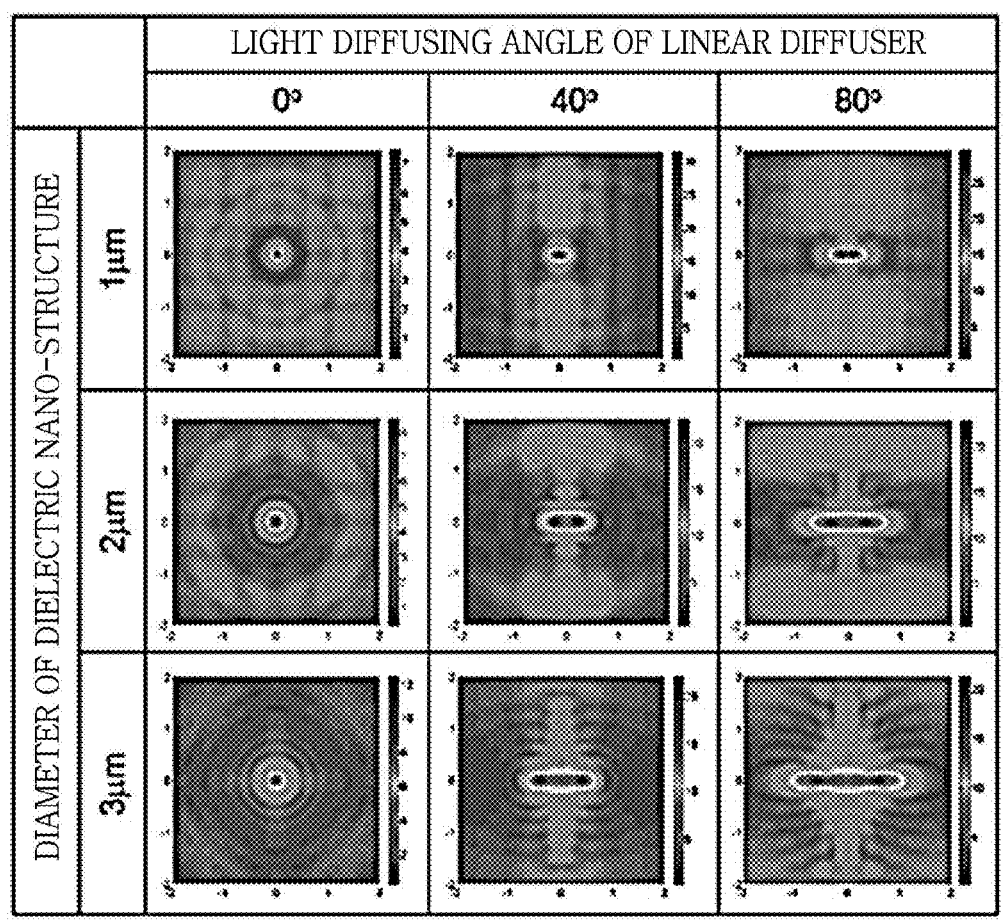
FIG. 2 shows a theoretical simulation result showing the photonic nanojet spot patterns depending on a light diffusing angle of a linear diffuser and a diameter of a dielectric microstructure.

FIG. 2 shows a theoretical simulation result showing how the focused spot pattern, formed at the lower exit plane of the dielectric microstructure when the light passing through the linear diffuser is focused by the dielectric microstructure, depends on light diffusing angle of the linear diffuser and a diameter of the dielectric microstructure. The calculation was performed using the finite-difference time-domain method (FDTD) assuming Polystyrene as a material of the dielectric microstructure and the light wavelength as 405 nm.

Referring to FIG. 2, the spot pattern of the photonic nanojet formed when the linear diffuser has a light diffusing angle of 0° is circular and has a constant size regardless of the diameter of the spherical polystyrene bead. If the light diffusing angle of the linear diffuser increases to 40° or 80°, the spot pattern becomes anisotropic like a shape of nanorod in proportion thereto in which the long axis is in a light diffusing direction of the linear diffuser. It should be noted that when the light diffusing angle of the linear diffuser is kept unchanged, the length of the anisotropic spot pattern in the long axis direction increases as the diameter of the polystyrene bead increases, while the short-axis length perpendicular to the light diffusing angle seems to change little. Practically considering that the length of the anisotropic spot pattern in the long axis direction cannot be greater than the diameter of the polystyrene bead, this means that the maximum value of the aspect ratio of the anisotropic spot pattern is determined by the diameter of the polystyrene bead used.

Figure 3:
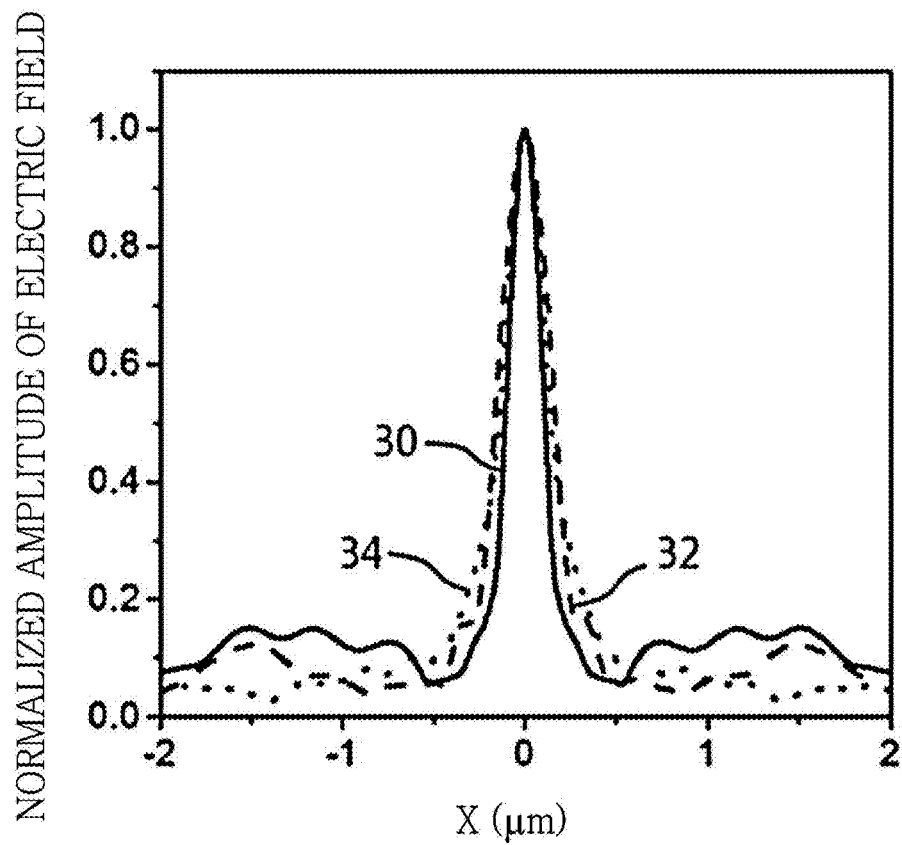
FIG. 3 shows the electric field amplitude distribution curves of photonic nanojet spot patterns in a short axis direction according to the diameter of the dielectric microstructure.
Figure 4:
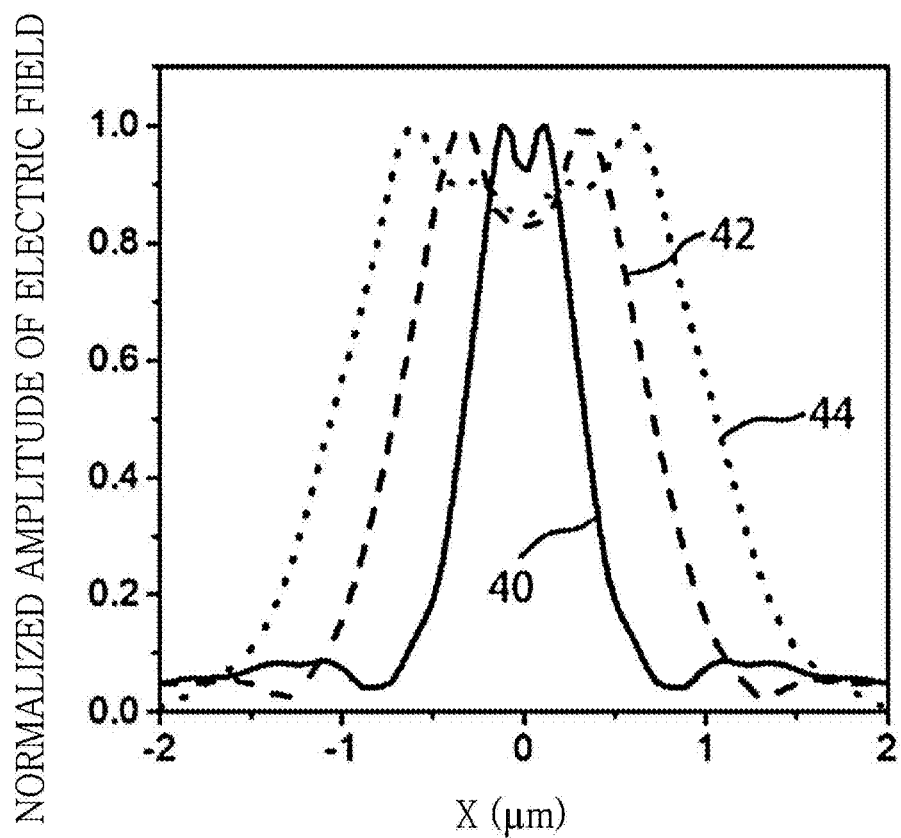
FIG. 4 shows the electric field amplitude distribution curves of photonic nanojet spot patterns in a long axis direction according to the diameter of the dielectric microstructure.

For more quantitative analysis, the line profiles of electric field amplitude distribution along a short axis and a long axis crossing the center point of the spot pattern are extracted from the case using a linear diffuser having a light diffusing angle of 80° in a two-dimensional contour map of FIG. 2 and shown in FIGS. 3 and 4, respectively for each diameter of beads.

FIG. 3 shows the line profiles of electric field amplitude distribution of the anisotropic spot pattern in a short axis direction. The electric field distributions look very similar regardless of the size of the polystyrene bead which increases from 1 μm (30) to 2 μm (32) and 3 μm (34), and hence the FWHM remains almost constant.

Meanwhile, the electric field amplitude distribution curves of the spot patterns in a long axis direction as shown in FIG. 4 show that as the size of the polystyrene bead increases from 1 μm (40) to 2 μm (42) and 3 μm (44), the FWHM of the curve increases in direct proportion thereto.

Figure 5:
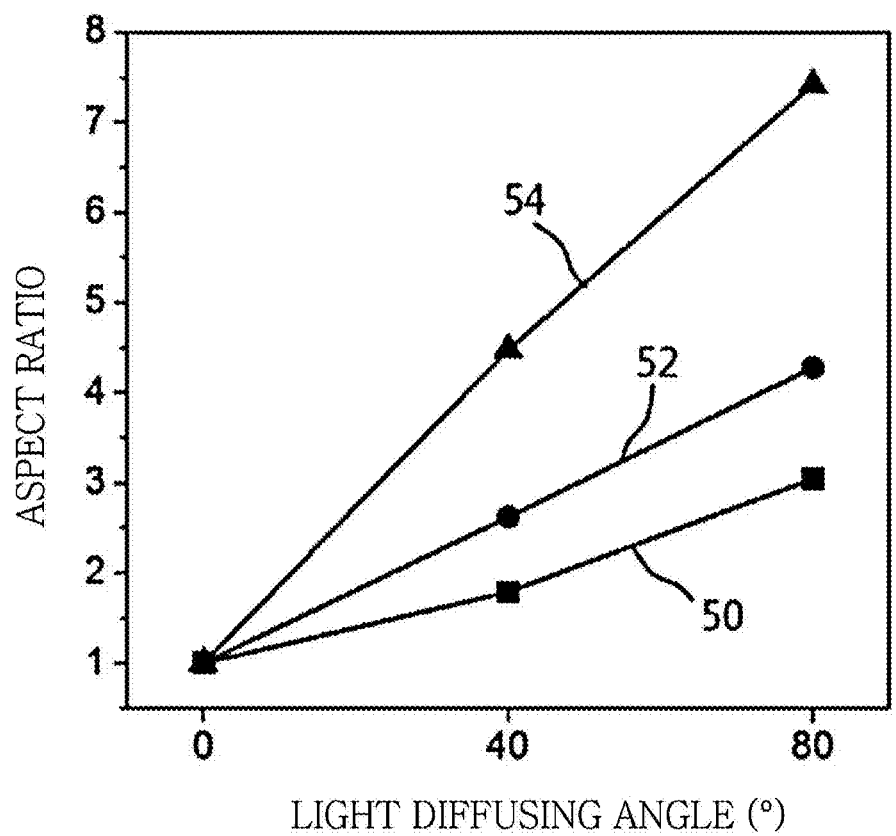
FIG. 5 is a graph showing the aspect ratio of a photonic nanojet spot pattern as a function of a light diffusing angle of a linear diffuser and a diameter of a dielectric microstructure.

In order to calculate the aspect ratio of spot patterns for nine cases depicted in FIG. 2, the line profiles of electric field amplitude along the long axis and the short axis are extracted for each case where the linear diffuser has a light diffusing angle of 0°, 40° and 80°, and the aspect ratio was evaluated as a relative ratio of the FWHM of the line profiles along the long axis to that along the short axis. FIG. 5 shows the aspect ratio of the spot patterns as a function of diameter of the polystyrene bead used. When the polystyrene bead has a diameter of 1 μm (50), it may be found that the maximum aspect ratio is just about 3 even when the linear diffuser of a diffusing angle of 80° is used. Here, the aspect ratio also increases as the light diffusing angle of the linear diffuser increases. However, when the linear diffuser has a light diffusing angle of 80° or above, the diffused light is not focused into a bead but overlaps with adjacent beads, thereby not contributing to the increase of the aspect ratio. Therefore, considering the fact that the FWHM of the spot patterns in the short axis direction is actually fixed to 250 nm to 300 nm, the effective way of further increasing the aspect ratio of the spot pattern is to increase the diameter of beads used. As shown in FIG. 5, as the bead diameter increases to 2 μm (52) and 3 μm (54), the aspect ratio of the spot pattern achievable at a specific light diffusing angle of the linear diffuser was also increased proportionally. When the bead has a diameter of 3 μm (54), it is found that the aspect ratio approaches the maximum up to about 7.4 when using a linear diffuser having a light diffusing angle of 80°.

Figure 6A:
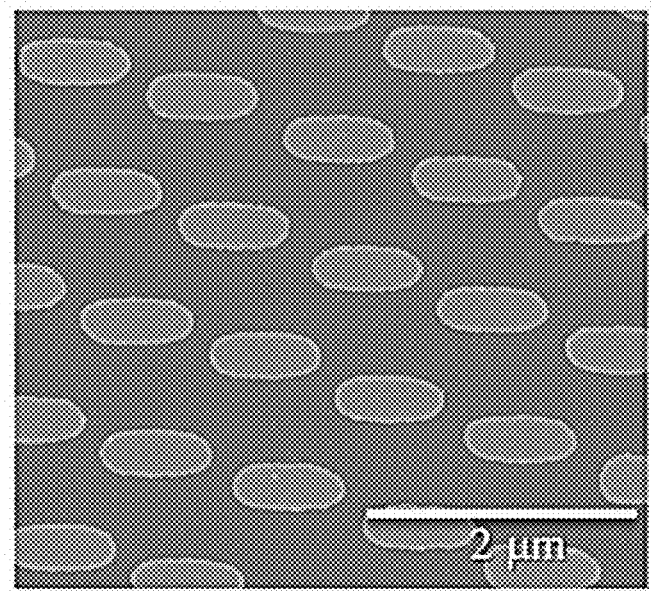
FIG. 6a shows a plasmonic Au nanoantenna array fabricated using a dielectric microstructure having a diameter of 1 μm according to an embodiment of the present disclosure.
Figure 6B:
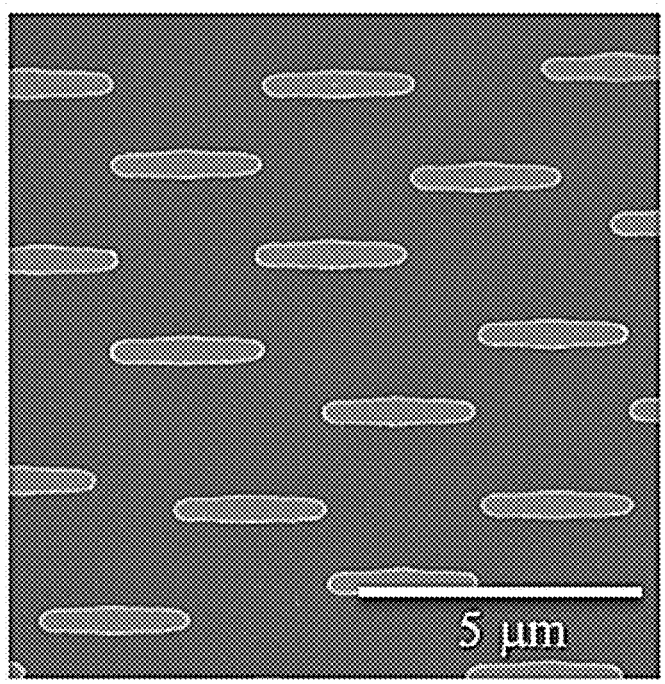
FIG. 6b shows a plasmonic Au nanoantenna array fabricated using a dielectric microstructure having a diameter of 3 μm according to an embodiment of the present disclosure.

Inventors have conducted experiments to fabricate a nanorod type plasmonic nanoantenna array having such a high aspect ratio so that its plasmonic resonance wavelength lies in an infrared wavelength region, by using the fact that the aspect ratio of the spot pattern effectively increases further according to the increase of the bead diameter, as expected from a computational simulation result. FIGS. 6a and 6b show scanning electron microscope (SEM) images of the nanorod type plasmonic Au nanoantenna arrays fabricated using an array of polystyrene microstructures with a diameter of 1 μm and 3 μm respectively as the focusing layer and also using a linear diffuser having a light diffusing angle of 80°.

Silicon was used as a material of the substrate, and a resist layer having a dual-layered structure was employed by sequentially coating an undercut-forming layer (LOL™ 2000) and a positive photoresist layer (AZ5214E) on the substrate with a thickness of 150 nm for each by means of spin coating. A monolayer of polystyrene beads array used as the focusing layer was formed with a hexagonal close-packed structure on the resist layer by means of a convective self-assembly method. The exposure process was then performed with an illuminating light of 405 nm wavelength, adjusting the exposure time, while the light intensity was set to be 1.2 mW/cm$^2$ low enough to prevent unnecessary sensitization of photoresist (PR) in a non-focused area. The exposure time was adjusted in consideration of the difference in intensity of focused light depending on a bead diameter so that the overall size of the pattern does not excessively increases due to excessive exposure. When using a polystyrene bead having a diameter of 1 μm (FIG. 5), the exposure time was set to 20 seconds, and for the bead of 3 μm diameter (FIG. 6), it was reduced to 10 seconds. After polystyrene beads were removed from the exposed sample by ultrasonic cleaning, a developing process was carried out using an AZ300MIF developer to remove the sensitized region of resist by the photonic nanojet.

According to an embodiment, after forming the pattern and before depositing a material suitable for plasmonic resonance, an adhesion layer may be formed on the substrate and the patterned resist layer. In this experiment, a 5-nm thickness Ti adhesion layer and a 50-nm Au thin film were sequentially deposited on the substrate exposed through the openings created in the resist layer and on the patterned resist layer by E-beam evaporation. The adhesion layer may be made of Cr, TiN, ZnS—SiO$_2$ or transparent conductive oxide, instead of Ti. The final lift-off process was completed by immersing the sample in acetone for 10 minutes to remove the photoresist layer and in an AZ300MIF developer for about a day to remove the undercut-forming layer.

As shown in FIGS. 6a and 6b, it may be found that even though the linear diffuser having a light diffusing angle of 80° is used identically, as the diameter of the polystyrene bead used as a focusing layer increases from 1 μm to 3 μm, the aspect ratio of the nanorod type plasmonic Au nanoantenna greatly increases from 2.5 to above 6.

Figure 7:
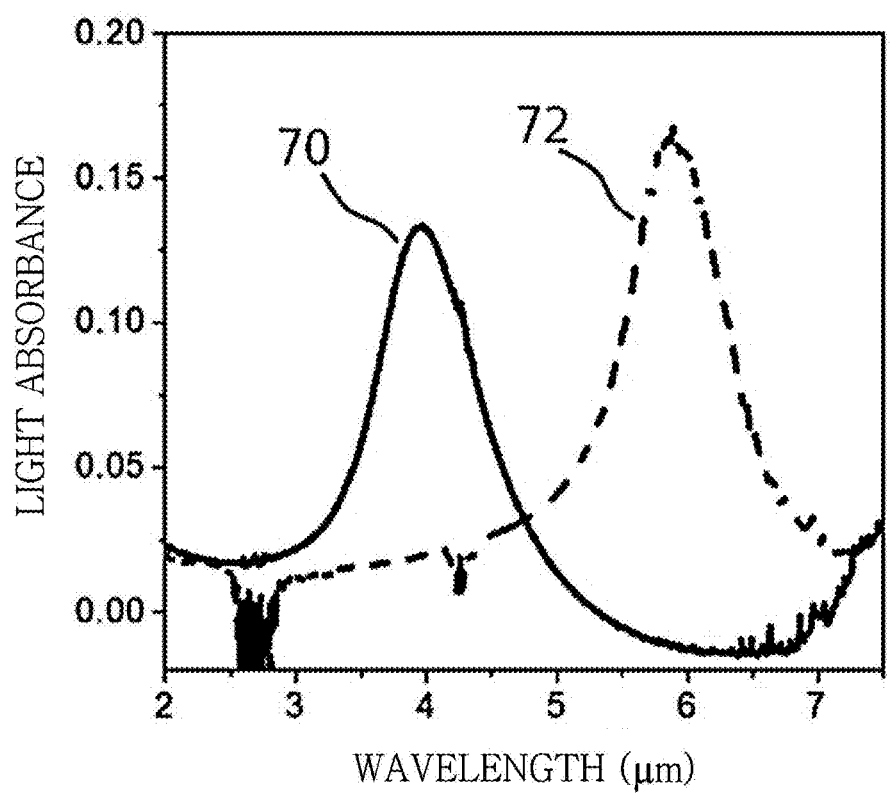
FIG. 7 shows the infrared absorbance curves of plasmonic Au nanoantenna arrays fabricated on a sapphire substrate according to an embodiment of the present disclosure.

FIG. 7 shows infrared absorbance spectra of the plasmonic Au nanoantenna arrays fabricated on sapphire substrates using an array of polystyrene beads having a diameter of 2 μm (70) and 3 μm (72) according to the process used for samples of FIG. 6. The infrared absorbance spectrum was obtained using the equation of log (1/T), which represents the optical absorbance, from the transmittance (T) measured by a Fourier transform infrared spectroscopy (FTIR). The linear diffuser with a light diffusing angle of 80° was used in the process. For the FTIR measurement, the incident light polarization was adjusted to be parallel to the long axis of Au nanoantennas using a KRS-5 wire-grid infrared polarizer. The SEM image analysis shows the mean aspect ratios of 4.3 and 6 for the Au nanoantennas fabricated using beads with a diameter of 2 μm (70) and 3 μm (72), respectively. Due to such a high aspect ratio, it was found that the fabricated Au nanoantenna array has a localized surface plasmon resonance wavelength in a mid-infrared region of 2 μm or above, and as the aspect ratio increases from 4.3 to 6, the wavelength of resonant absorption also greatly red-shifts from 3.96 μm to 5.89 μm.

Figure 8:
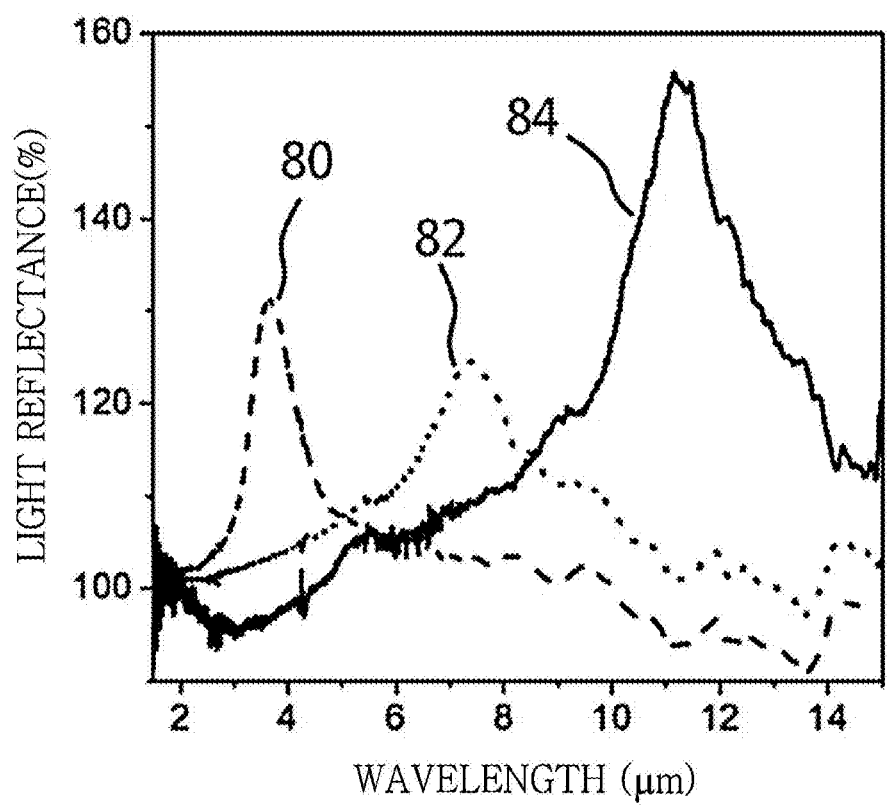
FIG. 8 shows the infrared reflectance curves of plasmonic Au nanoantenna arrays fabricated on a Si substrate according to an embodiment of the present disclosure.

FIG. 8 shows the plasmonic light reflectance curves of Au nanoantenna arrays fabricated on a silicon substrate of high dielectric constant using a linear diffuser with a light diffusing angle of 80° and polystyrene beads with different diameters of 1 μm (80), 2 μm (82) and 3 μm (84), respectively. It may be found that as the diameter of the polystyrene bead increases, the resonance wavelength also red-shifts from 3.65 μm (80) to 7.38 μm (82) and 11.25 μm (84) in proportion thereto. Here, the optical reflectance represents a relative reflectance of the nanoantenna array compared to the reflectance of the silicon substrate itself. Since the plasmonic nanoantenna exhibits a strong optical scattering as well as optical absorption at the resonance wavelength, higher optical reflectance is obtained in comparison to that of silicon substrate. Compared with FIG. 7, it may be understood that the plasmonic resonance wavelength may be shifted to the infrared region more greatly by increasing a dielectric constant of a supporting substrate even for the nanoantenna arrays of the same aspect ratio.

Figure 9:
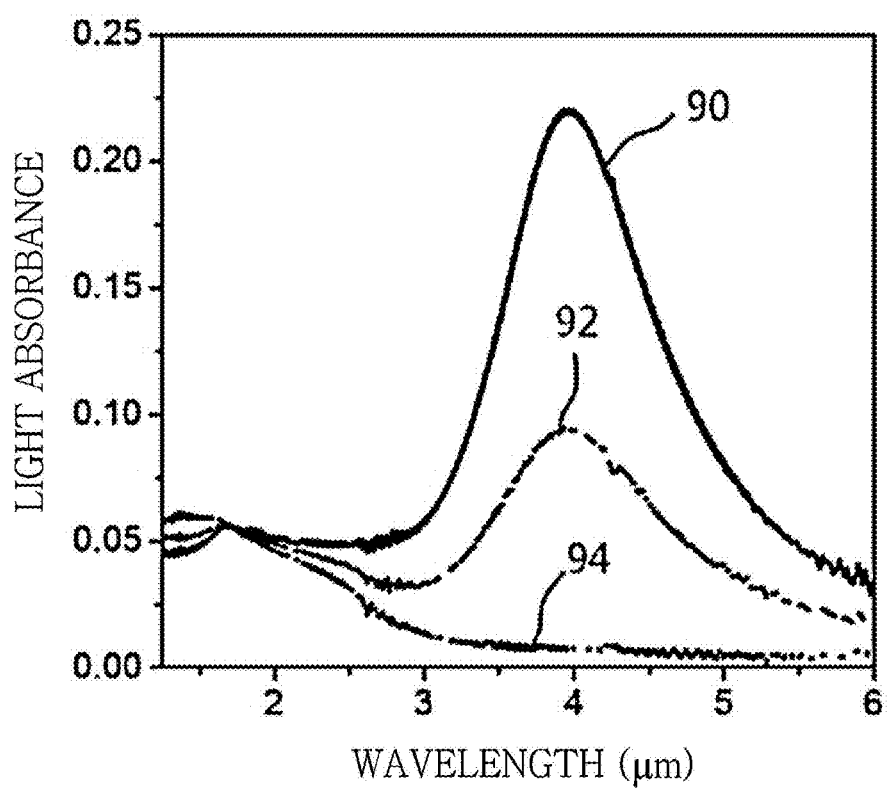
FIG. 9 shows the polarization dependence of an optical absorbance curve for the rod-type Au nanoantenna according to an embodiment of the present disclosure.

Since the nanorod type plasmonic nanoantenna generally exhibits polarization dependence, it may be proven that the nanorod type plasmonic nanoantenna operating in the infrared region is successfully fabricated according to the process according to an embodiment of the present disclosure by checking the polarization dependence of the nanoantenna. FIG. 9 shows the result for polarization dependence of a plasmonic light absorbance spectrum of the Au nanoantenna fabricated to have an aspect ratio of 4.3 on a sapphire substrate as shown in FIG. 7. When the long axis of the Au nanoantenna is parallel to the polarization direction of the polarizer (90), an optical absorbance peak is clearly observed due to the excitation of longitudinal mode of localized surface plasmon. Meanwhile, it is also found that the absorbance peak due to the plasmonic resonance in the longitudinal mode decreases almost by half when the polarizer rotates by an angle of 45° (92), and disappears if the polarization direction of the polarizer becomes perpendicular to the long axis direction of the nanoantenna (94). In other words, since the nanoantenna array fabricated by the nanoantenna array fabricating method according to an embodiment of the present disclosure exhibits polarization dependence, it may be proved that the nanorod type plasmonic nanoantenna array is successfully fabricated.

From the above, it may be confirmed that the nanoantenna array fabricating method including a diffuse photonic nanojet lithography process according to an embodiment of the present disclosure is very useful for making a plasmonic infrared nanoantenna array having a plasmonic resonance wavelength in an infrared region. In addition, it is possible to further expand the infrared wavelength band in which the plasmonic resonance of the nanoantenna may be implemented, by increasing the diameter of the focusing bead used in the process, decreasing the thickness of the plasmonic metal film deposited, or increasing a dielectric constant of the substrate material.

Meanwhile, if the nanoantenna array fabricating method of an embodiment is used, the spatial orientation of the nanoantenna array may be arbitrarily controlled by a simple process of rotating the light diffusing direction of the linear diffuser to a desired azimuth in the exposure process.

Figure 10A:
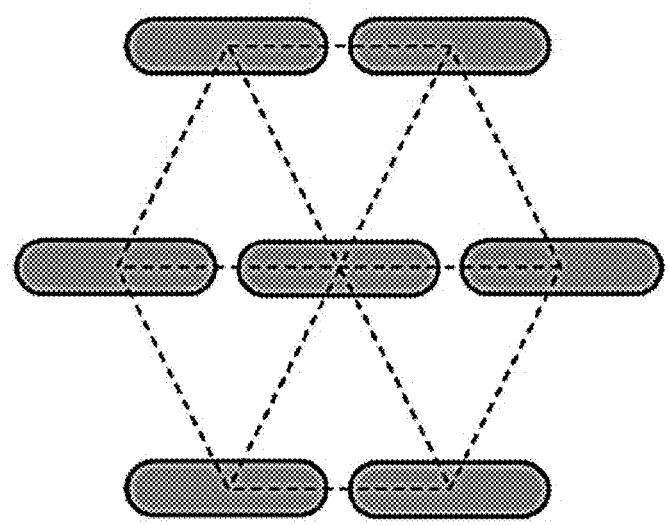
FIG. 10a shows spatial orientation distribution of a nanoantenna array fabricated by the nanoantenna array fabricating method according to an embodiment of the present disclosure.
Figure 10B:
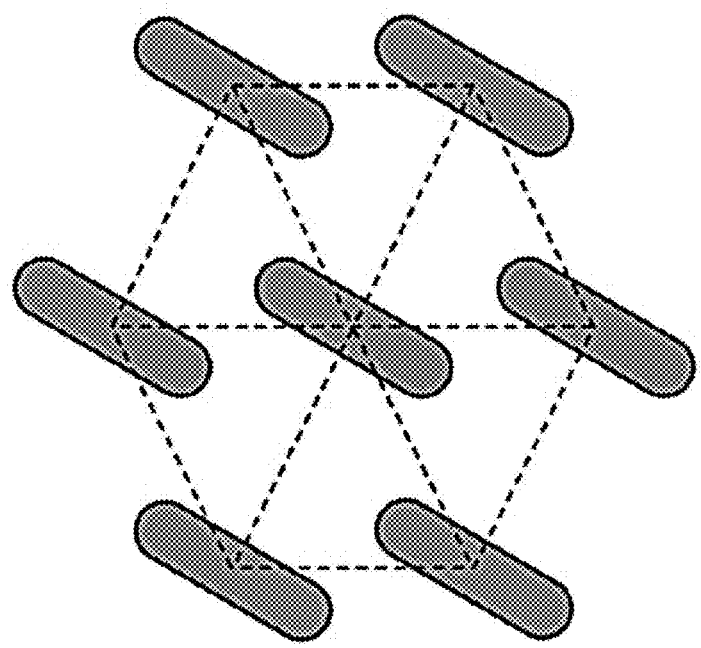
FIG. 10b shows spatial orientation distribution of a nanoantenna array fabricated by the nanoantenna array fabricating method according to another embodiment of the present disclosure.

FIGS. 10*a* and 10*b* show the examples of orientational distribution of nano-antenna arrays which may be fabricated through the same exposure processes except for the light diffusing direction of the linear diffuser. The dielectric microstructure array formed on a resist layer by self-assembly method has a hexagonal close-packed structure. As shown in FIG. 10*a*, if the light diffusing direction of the linear diffuser is aligned in a row direction at which the dielectric microstructures are closely packed, the fabricated nanoantenna array has a structure in which long axes of adjacent nanoantennas are on the same line. In this case, the gap between the nanoantennas may be controlled with a relatively great degree of freedom by controlling the aspect ratio of the nanoantennas. Such gap control may be used for causing dipolar coupling between infrared nanoantennas or inducing a tip-to-tip type strong enhancement of local electric field at the nano gap.

Meanwhile, FIG. 10*b* shows the orientational distribution of a nanoantennas array which may be fabricated when the light diffusing direction of the linear diffuser makes an angle of 30° with respect to the close-packed row. Differently from FIG. 10*a*, the fabricated antenna array has a structure in which long axes of adjacent nanoantennas are on different lines and the individual nanoantennas are well separated from each other.

Figure 11A:
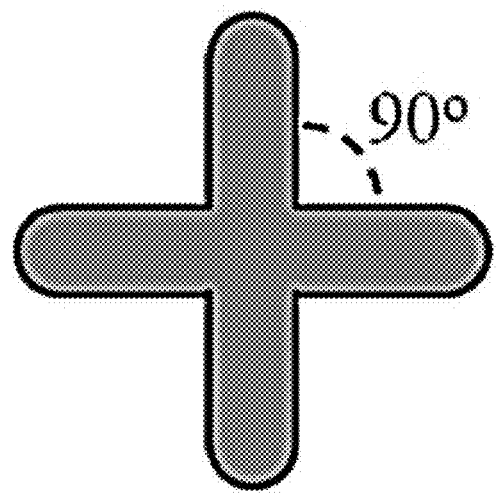
FIG. 11a shows a nanoantenna of a nanostar structure according to an embodiment of the present disclosure.
Figure 11B:
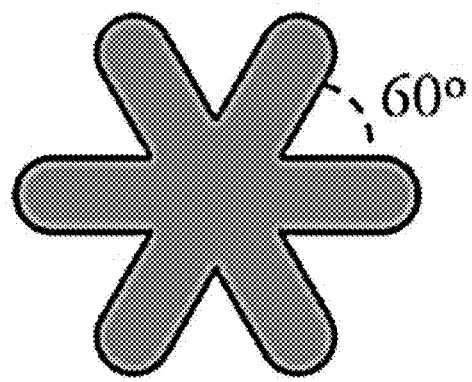
FIG. 11b shows a nanoantenna of a nanostar structure according to another embodiment of the present disclosure.

By using the fact that the spatial orientation of the nanoantenna array may be controlled by adjusting the light diffusing direction of the linear diffuser, the nanoantenna array fabricating method of an embodiment may form a nanoantenna array having a nanostar structure which includes a plurality of arms by repeating only the step of exposure process multiple times just rotating the light diffusing direction of the linear diffuser in each time. FIG. 11*a* shows a nanostar structure achievable when a second exposure process is performed with a light diffusing direction of the linear diffuser rotated by 90° after a first exposure process. FIG. 11*b* shows an example of nanostar structure achievable when a triple exposure process is performed while rotating only the linear diffuser by an angle of 60° in successive exposure processes. The relative angles between adjacent arms of the nanostar structure may be arbitrarily controlled. Unlike the nanorod type structure, the nanoantenna array of the nanostar structure may control polarization dependence and bring about the increased effective density of its constituent nanorod antennas per unit area.

Figure 12:
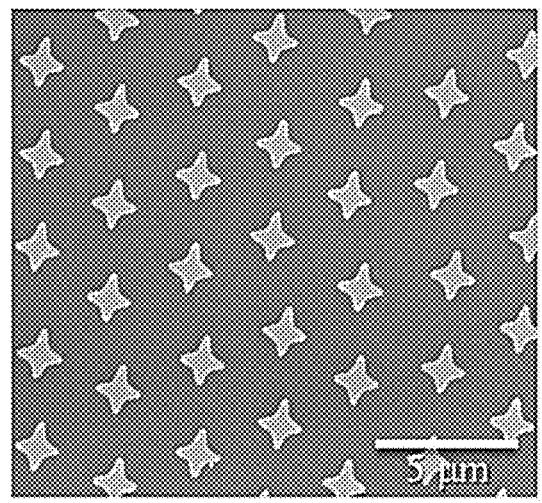

FIG. 12 is a SEM image showing the nanostar type Au nanoantenna array fabricated by applying a double exposure process as explained with regard to FIG. 11*a*. Sapphire substrate was used and the process was performed by using an array of polystyrene beads having a diameter of 3 μm as the focusing layer and a linear diffuser having a light diffusing angle of 80°. In both the first and second exposure processes, the exposure time was fixed to 9 seconds. The second exposure process was performed after rotating only the light diffusing direction of the linear diffuser by 90° after the first exposure process. Referring to FIG. 12, it was confirmed that an array of nanostar type Au antennas with four arms of a 90° rotational symmetry was successfully fabricated.

Figure 13:
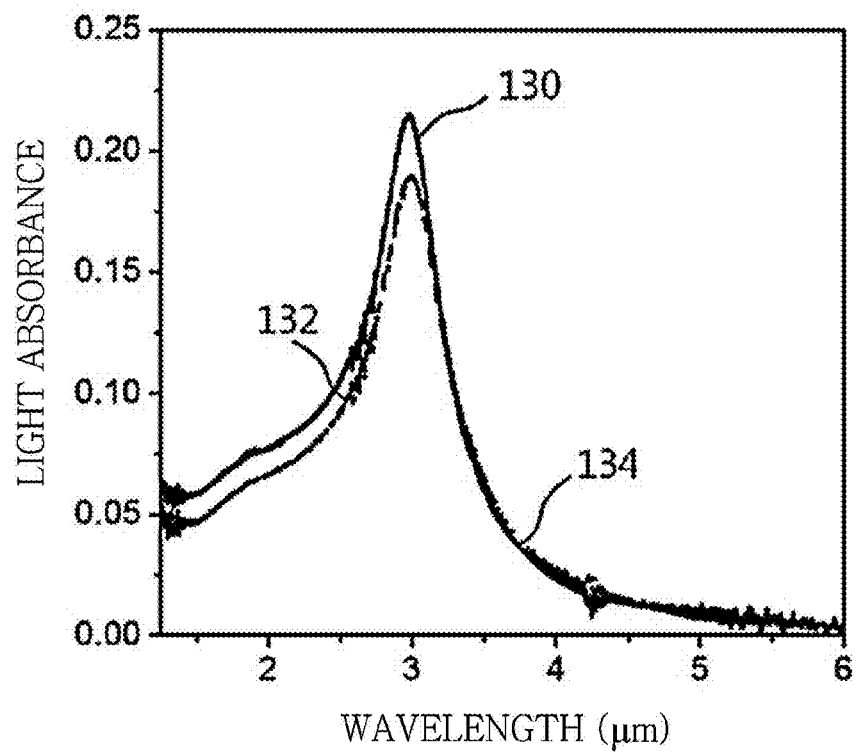
FIG. 13 shows the polarization dependence of an infrared absorbance curve measured for the nanostar type Au nanoantenna of FIG. 12.

FIG. 13 shows the polarization dependence of infrared optical absorption spectrum measured for the nanostar type Au nanoantenna shown in FIG. 12. Contrary to the case of nanorod type shown in FIG. 9, the optical absorbance spectrum due to the localized surface plasmon resonance maintains almost the same curve shape regardless of the incident light polarization which rotated by 45° (132) or 90° (134) with respect to the angle (130) parallel to any arm of the nanostar. This is ascribed to the rotational symmetry of the nanostar type Au nanoantenna having the structure of FIG. 12, and it was confirmed that the fabricated nanostar type Au nanoantenna has no polarization dependence. Since the polarization independence helps to consistently keep the profile of plasmonic resonance light absorbance curve regardless of the incident light polarization and even for random-polarized light, in practical viewpoint, there is an additional advantage in that an expensive infrared linear polarizer may not be used.

In addition, according to an embodiment of the present disclosure, the plasmonic nanoantenna array chip fabricated to operate in an infrared wavelength region by depositing a material suitable for plasmonic resonance onto a resist layer patterned to have an anisotropic pore structure of a high aspect ratio in it, may be used as a plasmonic substrate for an infrared spectroscopy for highly sensitive and selective detection of various biochemical molecules or a refractive-index sensing based plasmonic sensor chip operating in an infrared wavelength region.

Figure 14:
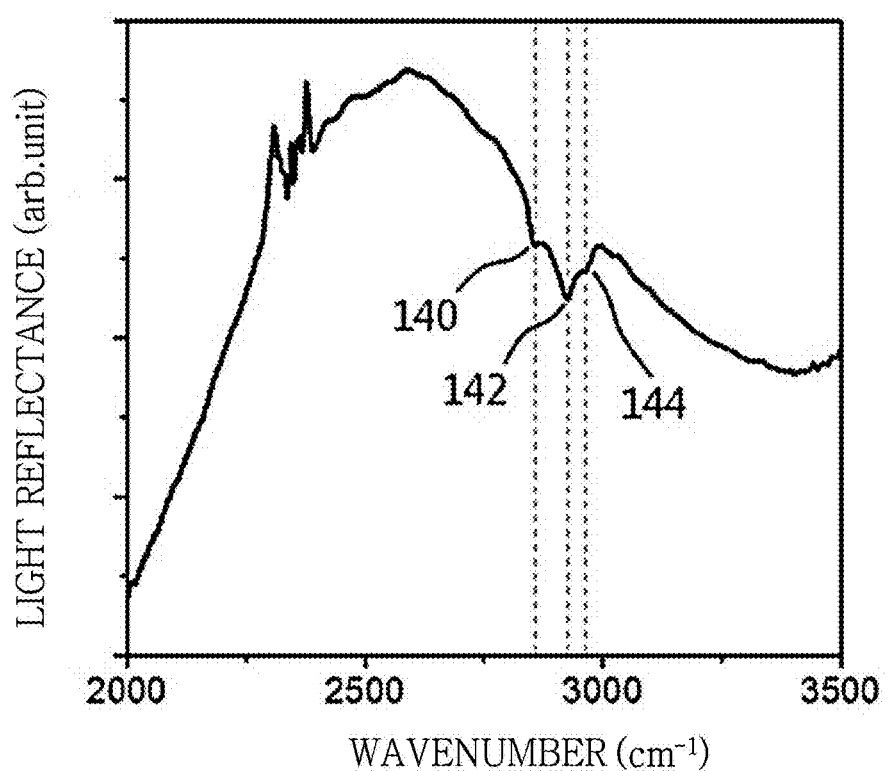
FIG. 14 shows an optical reflectance curve of the nanoantenna array chip fabricated for use as a plasmonic substrate for surface-enhanced infrared absorption spectroscopy according to an embodiment of the present disclosure.

FIG. 14 shows an optical reflectance spectrum of the nanoantenna array chip used for a plasmonic substrate for surface-enhanced infrared absorption (SEIRA) according to an embodiment of the present disclosure. Here, the optical reflectance represents a relative reflectance with respect to that of a reference mirror. An octadecanethiol (ODT) self-assembled monolayer (SAM) having a chemical rational formula of $CH_3(CH_2)_{17}SH$ was selected as a molecular model system. As known from the chemical rational formula, the ODT SAM has seventeen $CH_2$ bonds and one $CH_3$ bond. Since the $CH_2$ and $CH_3$ bonds have a characteristic infrared absorption in a frequency band of about 2900 $cm^{-1}$, namely near a wavelength of 3.45 μm due to a stretching vibrational mode, the experiment was performed using a nanorod type Au nanoantenna array chip having an aspect ratio of about 4, fabricated on a sapphire substrate to show a plasmonic resonance characteristic in the corresponding wavelength region. Here, the frequency represents a wave number expressed as a reciprocal of wavelength (1/λ). In order to form the ODT SAM on the surface of the Au nanoantenna, the nanoantenna array chip was immersed in a 1 mM ODT solution prepared in ethanol solvent for 24 hours. After that, washing and drying process were performed, and then the optical reflectance (R) spectrum was measured for the sample using a FTIR microscope.

Referring to FIG. 14, three small dips are clearly observed near a high-frequency side of the optical reflectance peak due to the surface plasmon resonance of the Au nanoantenna. The dip frequencies are 2855 $cm^{-1}$ (140), 2924 $cm^{-1}$ (142) and 2961 $cm^{-1}$ (144). It is thought that the first two observed in relatively low frequencies correspond to a symmetric and an asymmetric modes of stretching vibration of $CH_2$ bonds, respectively, and the other dip of highest frequency results from the infrared absorption due to an asymmetric mode of stretching vibration of a $CH_3$ bond. The ODT single molecule is known to occupy an area of about 0.2 $nm^2$ when being self-assembled into a close-packed structure. Therefore, considering the area of the nanoantenna used in this experiment, there exist about 5.7 attomole of molecules per unit nanoantenna. In particular, since the observed infrared absorption is dominated by ODT molecules present at both end-tip regions of the nanoantenna where the local electric field is concentrated, it may be assumed that only a small amount of molecules as low as about 1 attomole contributes to actual infrared absorption. Therefore, since the infrared nanoantenna according to an embodiment of the present disclosure has a high aspect ratio, it may be understood that the local electric fields concentrated to both end-tips have very strong intensity and thus the enhancement effect of infrared absorption is excellent. In particular, the clear detection of the asymmetric stretching vibration mode of $CH_3$ bond around a frequency of 2961 $cm^{-1}$ of which only one bond is included in the ODT SAM proves that the nanoantenna array chip according to an embodiment of the present disclosure is suitable for use as a plasmonic substrate amplifying the infrared spectroscopic signals for highly sensitive analysis of a small amount of molecules.

Figure 15:
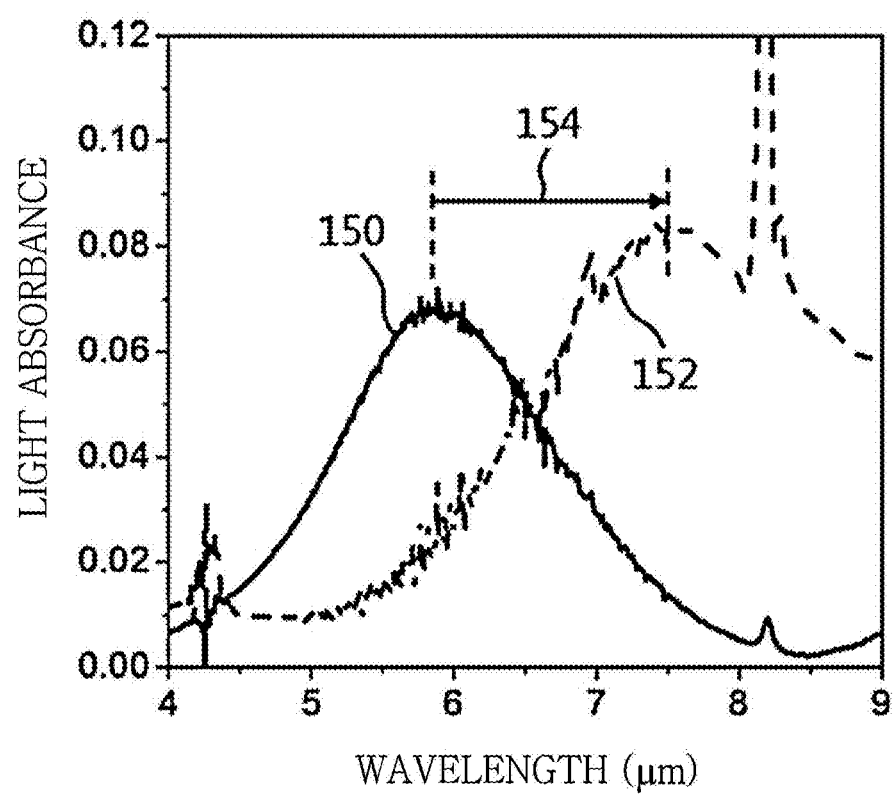
FIG. 15 shows an optical absorbance curve of the nanoantenna array chip fabricated for use as a refractive index sensor operating in an infrared wavelength region according to an embodiment of the present disclosure.

As another example, FIG. 15 shows the optical absorbance curves of the nanoantenna array chip when applied to a refractive index sensor operating in an infrared wavelength region, according to an embodiment of the present disclosure. FIG. 15 shows the change in optical absorbance curves measured by a FTIR when an Au nanorod type antenna array chip having an aspect ratio of about 6 and fabricated on a $CaF_2$ substrate makes an interface with the air (150) and a chloroform ($CHCl_3$) solution (152) which is transparent at an infrared wavelength and having a refractive index of about 1.424. It was observed that a red-shift (154) of about 1.61 μm occurred when the chloroform solution covered the chip (152), compared with the initial state (150) at which the chip was in contact with air. When expressed as sensitivity defined by the change of resonance wavelength with respect to the change of a unit refractive index, a value of 3.79 μm/RIU was obtained. Considering the bulk sensitivity of nanoantennas working in a visible region is around several hundred nm/RIU, it is thought that the sensitivity of the plasmonic infrared nanoantenna is remarkably high. In addition, since the decay length into the surrounding medium of the localized surface plasmon excited in the infrared region reaches several μm, a cell-based measurement may be possible.

Since various changes or modifications can be made to the present disclosure without departing from the scope of the present disclosure by those skilled in the art, the present disclosure is not limited to the above embodiments or the accompanying drawings.

What is claimed is:

1. A method for fabricating a nanoantenna array, comprising:
    forming a resist layer on a substrate;
    forming a focusing layer having a dielectric microstructure array on the resist layer;
    diffusing light in a specific direction by using a linear diffuser;
    forming an anisotropic pattern on the resist layer by illuminating the light diffused by the linear diffuser on the focusing layer and the resist layer;
    depositing a material suitable for a plasmonic resonance onto the substrate and the resist layer on which the pattern is formed;
    forming a nanoantenna array on the substrate by removing the resist layer and the material deposited on the resist layer; and
    determining a size of the dielectric microstructure based on an aspect ratio of the pattern to be formed.

2. The method for fabricating a nanoantenna array according to claim 1,
    wherein the dielectric microstructure has a diameter of 1 μm to 10 μm.

3. The method for fabricating a nanoantenna array according to claim 1,
    wherein the nanoantenna has a resonance wavelength of 2 μm or greater.

4. The method for fabricating a nanoantenna array according to claim 1,
wherein the diffusing of light in the specific direction and the forming of the anisotropic pattern are repeated a plurality of times, and
wherein the light diffusing direction of the linear diffuser is changed whenever the diffusing of light in the specific direction and the forming of the anisotropic pattern are performed.

5. The method for fabricating a nanoantenna array according to claim 4,
wherein the nanoantenna has a plurality of arms.

6. The method for fabricating a nanoantenna array according to claim 1,
wherein the nanoantenna array has a two-dimensional hexagonal close-packed structure.

7. The method for fabricating a nanoantenna array according to claim 1,
wherein the substrate is made of sapphire, CaF2, MgF2, ZnSe, Si, Si3N4, Ge, GaAs, SiO2, KBr, diamond or polymer.

8. The method for fabricating a nanoantenna array according to claim 1,
wherein the nanoantenna is made of a material whose optical behavior in an infrared wavelength region is described with a free electron model.

9. The method for fabricating a nanoantenna array according to claim 8,
wherein the nanoantenna is made of Au, Ag, Cu, Al, Pt, Pd, Ni, Co, Fe, Mn, Cr, Mo, W, V, Ta, Nb, Sn, Pb, Sb, Bi, or their alloys.

10. The method for fabricating a nanoantenna array according to claim 8,
wherein the nanoantenna is made of a semiconducting material having a free electron density of 10-20 cm-3 or above.

11. The method for fabricating a nanoantenna array according to claim 1, after the forming of the anisotropic pattern and before the depositing of the material, further comprising:
forming an adhesion layer on the substrate and the resist layer on which the pattern is formed.

12. The method for fabricating a nanoantenna array according to claim 11,
wherein the adhesion layer is made of Ti, Cr, TiN, ZnS-SiO2 or transparent conductive oxide.

13. The method for fabricating a nanoantenna array according to claim 1, wherein the aspect ratio of the pattern to be formed is 4 or greater.

14. The method for fabricating a nanoantenna array according to claim 1, further comprising determining a light diffusing angle of the linear diffuser based on the aspect ratio of the pattern to be formed.

15. A structure for lithography, comprising:
a linear diffuser configured to diffuse light in a specific direction;
a focusing layer including a dielectric microstructure array comprising beads and configured to focus the light diffused by the linear diffuser; and
a resist layer disposed to have an anisotropic pattern formed by being illuminated by the light focused by the focusing layer,
wherein an aspect ratio of the pattern to be formed is based on the specific direction of the diffused light and a diameter of the beads.

16. The structure for lithography according to claim 15,
wherein the dielectric microstructure array has a two-dimensional hexagonal close-packed structure.

17. The structure for lithography according to claim 15,
wherein a light diffusing angle of the linear diffuser is determined based on an aspect ratio of the pattern to be formed.

18. The structure for lithography according to claim 13,
wherein the dielectric microstructure has a diameter greater than 1 μm.

* * * * *